(12) United States Patent
Damaria et al.

(10) Patent No.: US 6,811,790 B1
(45) Date of Patent: Nov. 2, 2004

(54) STORAGE STABLE PESTICIDE FORMULATIONS CONTAINING AZADIRACHTIN

(75) Inventors: Sreenivasa Rao Damaria, Bangalore (IN); Srinivasa Sridhar, Bangalore (IN); Krishnasami Raman, Chennai (IN); Mambully Chandrasekaran Gopinathan, Bangalore (IN)

(73) Assignee: E.I.D. Parry (India) Ltd., Bangalore (IN)

( * ) Notice: Subject to any disclaimer, the term of this patent is extended or adjusted under 35 U.S.C. 154(b) by 0 days.

(21) Appl. No.: 09/536,351

(22) Filed: Mar. 27, 2000

(51) Int. Cl.$^7$ .......................... A01N 25/32; A01N 65/00
(52) U.S. Cl. .................... 424/406; 424/195.1; 424/405; 424/761; 514/27
(58) Field of Search .............................. 424/405, 195.1, 424/761, 406; 426/330.6, 334, 655; 514/27, 28

(56) References Cited

U.S. PATENT DOCUMENTS

| | | | |
|---|---|---|---|
| 4,556,562 A | 12/1985 | Larson | 424/195.1 |
| 4,946,681 A | 8/1990 | Walter | 424/195.1 |
| 5,001,146 A | 3/1991 | Carter et al. | 494/195.1 |
| 5,124,349 A | 6/1992 | Carter et al. | 514/453 |
| 5,281,618 A | 1/1994 | Walter | 514/453 |
| 5,352,697 A | 10/1994 | Butler et al. | 514/468 |
| 5,372,817 A | 12/1994 | Locke et al. | 424/405 |
| 5,405,612 A | 4/1995 | Locke et al. | 424/410 |
| 5,409,708 A | 4/1995 | Locke et al. | 424/410 |
| 5,503,837 A | 4/1996 | Roland et al. | 424/405 |
| 5,635,193 A | 6/1997 | Walter | 424/405 |
| 5,695,763 A | 12/1997 | Kleeberg | 424/195.1 |
| 5,730,986 A | 3/1998 | Bandyopadhyay et al. | 424/195.1 |
| 5,736,145 A | 4/1998 | Murali | 424/195.1 |
| 5,827,521 A | 10/1998 | Moorthy | 424/405 |
| 5,856,526 A | 1/1999 | Sankaram et al. | 549/348 |
| 5,885,600 A * | 3/1999 | Blum et al. | 424/405 |
| 6,034,128 A * | 3/2000 | Ujihara | 514/531 |

FOREIGN PATENT DOCUMENTS

| | | | | |
|---|---|---|---|---|
| EP | 0 579 624 B1 | 3/1992 | | A01N/65/00 |
| IN | 181845 | 8/1995 | | |
| IN | MAS/1855 | 8/1997 | | |
| WO | WO 92/16109 | 10/1992 | | A01N/65/00 |

OTHER PUBLICATIONS

Milks—Practical Veterinary Pharmacology p. 260, 261, 1949.*

Dimetry, et al., "Synergistic effect of some additives on the biological activity and toxicity of neem–based formulations against the cowpea aphid, Aphis craccivora Koch", Insect Sci. Applic., 17(3/4): 395–99 (1997).

Schauer, "Effects of variously formulated neem seed extracts on Acrythosiphon pisum and Aphis fabae", Proc. $2^{nd}$ Int. Neem Conf. (Sauischholzhausen), pp. 141–50 (1983).

Parmar et al., "Neem oil as a synergist for insecticides," Neem Newsletter, 3:3–5 (1986).

Dureja et al., "Stability of Azadirachtin–A in different organic solvents and acqueous solution," Pesticide Research Journal, 11(1):90–92 (1999).

Rembold et al., "Azadirachums: Structure and Activity relations in case of Epilachna varivestis," In The Neem Tree Azadirachta indica A. Juss. And other meliaceous plants: Sources of unique natural products for integrated pest management, medicine, industry, and other purposes, Ed. Schmutterer, VCH Verlagsgesellschaft, Weinheim (FRG), pp. 222–30 (1995).

Kleeberg et al., "Analytical determination of Azadirachtin A and Azadirachtin B in neem extracts," In: Practice Oriented Results on Use and Production of Neem Ingredients and Pheromones, Proceedings of the $3^{rd}$ Workshop, Ed H. Kleeberg, Duck & Graphic, Giessen, pp. 139–48, (1994).

* cited by examiner

Primary Examiner—Neil S. Levy
(74) Attorney, Agent, or Firm—Kilyk & Bowersox, P.L.L.C.

(57) ABSTRACT

A pesticide formulation is described which contains at least one vegetable oil, at least one surfactant, and at least one type of azadirachtin. Preferably, the vegetable oil is at least a sesame seed oil and the surfactant is at least a non-ionic surfactant. The pesticide formulations of the present invention are preferably storage stable and are environmentally safe since preferably no organic solvents are present in the formulations.

5 Claims, No Drawings

STORAGE STABLE PESTICIDE FORMULATIONS CONTAINING AZADIRACHTIN

BACKGROUND OF THE INVENTION

The present invention relates to pesticide formulations and more particularly relates to storage stable pesticide formulations containing azadirachtin.

Extracts of various parts of the neem tree (*Azadirachta indicia*) such as leaves, bark, seeds, etc. have been long known to have insecticide activity. The seed kernel, in particular, processes the most active limonoids, such as Azadirachtin A and B and structurally related compounds such as C, D, E, F, G, H, I, J, K, and the like, along with nimbin, salannin, azadiradione, and the like. All of the natural azadirachtins have been reported to have a very high growth disturbing activity against *Epilachna varivestis*, with $LC_{50}$s in the range of 0.3 to 2.8 ppm (H. Rembold and I Puhlmann, 1995). More than 100 terpenoid metabolites are reported from the neem seed/fruit of the neem tree. Various methods have been described to extract these active components in the crude or semi crude forms to be used in commercially acceptable vehicles in the form of liquid and solid formulations. The crude neem seed extracts obtained after removal of lipid components normally contain 20–45% of Azadirachtin A and B and have been shown to be potent insect growth regulators and feeding deterrent and form potential active ingredients in commercial pest control formulations. The active molecules of the neem seed extracts are rather large and complex, and having acid and base sensitive functional groups they tend to be unstable in these vehicles, thus posing a major limitation for commercial use of these extracts.

So far, azadirachtin has been widely formulated in liquid forms to be applied as an emulsion or solution to agriculture crops. Various organic solvents and other inorganic additives have been used as carriers in order to make a cost effective and efficacious delivery system. The use of such carriers is rather limited, however, since many solvents are deleterious to the stability of azadirachtin. Dureja (1999) has studied the degradation of azadirachtin A in various solvents for 25 days at 29+/−1° C. The results indicated 50% degradation of azadirachtin A in methanol and acetone, 75–80% degradation in methylene chloride, carbon tetrachloride and chloroform and about 80% degradation in ethanol and water.

Storage-stable azadirachtin formulations and methods of preparing stable azadirachtin compositions have been proposed. U.S. Pat. No. 4,556,562 reports that the stability of azadirachtin in ethanol emulsions increased by diluting the concentration of azadirachtin to between 2000 and 4000 ppm and adjusting the pH to between 3.5 and 6.0. U.S. Pat. No. 4,946,681 (Walter) reports greater stability for azadirachtin in solutions of aprotic solvents containing less than 2–5% of water. U.S. Pat. No. 5,001,146 indicates that azadirachtin stability is improved by adjusting the concentration of polar aprotic solvent to at least 50% by volume and by decreasing water content to less than 15% by volume. Moreover, U.S. Pat. No. 5,001,146 further indicates that azadirachtin stability depends upon the type of solvent employed, and that stability requires storage in large quantities of certain enumerated aprotic and alcohol solvents. Murali (U.S. Pat. No. 5,736,145) reports a storage stable aqueous composition containing azadirachtin A and U.S. Pat. No. 5,827,521 indicates a stable azadirachtin formulation containing aliphatic dihydroxylated alcohols of more than 80% by volume and optionally with sunscreens and antioxidants.

U.S. Pat. No. 5,352,697 describes the enhancement of stability of azadirachtin in solution by the presence of epoxide, preferably an epoxidized vegetable oil. These methods describe the enhancement of azadirachtin containing extracts in the liquid form prepared from neem seed kernel with organic solvents.

European Patent No. 9216109 describes making an extract of neem seed in solid form with greater stability. The stability of azadirachtin in neem extracts is reported to be improved by removing the lipid impurities from extracts (Indian Patent Application No. 1855). Walter (U.S. Pat. No. 5,635,193) reports that an azadirachtin containing solid is stable by limiting moisture and volatile polar solvents to less than 1% and 5%, respectively. A formulation containing 0.05% to 2% surfactant and 99% of solid diluent has been claimed as a stable bio-control agent by retention of at least 75% of azadirachtin after 2 weeks of storage at 54° C. Such a formulation may be used as a dust and wettable powder, but the efficacy of azadirachtins in such vehicular formulations is not practically reported.

Another formulation is a solid form of neem seed extract prepared from the kernel of neem seed as per the methods described in U.S. Pat. No. 5,695,763, European Patent No. 9,216,109, and IN 181,845. The product is quite stable with respect to its active ingredients viz Azadirachtin A, B, nimbin, salannin and the like.

Though, various extracts with stable Azadirachtin have been reported, stability of azadirachtin in a formulated state is still a concern. Azadirachtin is highly unstable in various surfactants, organic solvents, and in different combinations of solvent and surfactants in liquid formulations which is a serious limitation for the development of a shelf stable commercial product.

Normal pesticide formulations contain various solvents made mostly from petroleum, and there is a concern that usage of such solvents in specialty pesticide formulations, especially meant for organic farming, veterinary application, and the like, is discouraged. The use of such solvents, even at a lower rate, demands large amounts of surfactants and other additives which makes the cost of the formulations high. The use of a broader range of ingredients in liquid formulations and the associated problem of instability in such formulations is also a serious concern for the commercial success of azadirachtin containing crop protection agents. Accordingly, there is still a need for a formulation containing simple, safe, and cost effective vehicles which yet provides stable and efficacious products.

Various plant oils such as neem oil, castor oil, acorus oil, and sesame oil, have been used in specific end use applications as additives for enhancing the efficacy of formulations by synergism. These oils may be ideal substitutes to organic solvents but at higher concentrations these may cause phytotoxicity and instability to the active ingredients of the formulation. The advantage of sesame oil as a natural synergist to synthetic pyrethroid insecticides has been demonstrated. The possibility of increasing the efficacy of various neem seed extracts against different insects by addition of sesame oil has been examined. M. Schauer (1983) has reported that lecithin II with sesame oil has improved the effect of a neem extract obtained from methyl-tertiary-butyl-ether in achieving higher mortality of *Acyrthosiphon pisum* and *Aphis fabae*. N. Z. Dimetry et al. have reported that addition of sesame oil to commercial neem formulations containing azadirachtin has increased insecticide efficacy of the formulations against adult apids, *Aphis craccivora*. While these reports indicate that sesame oil may enhance the efficacy of neem extracts, no one has studied its effect on the stability of most active compounds of neem extracts such as azadirachtins which is an important aspect for development of commercial formulations.

Accordingly, there is a need to develop environmentally safe pesticide formulations which contain azadirachtin and which are further storage stable and economical.

One aim of the present invention is to develop a delivery system for azadirachtin containing neem seed extracts, free from any solvent, less expensive, and completely soluble in water.

The present invention provides a composition of a neem seed extract and sesame oil, free from any organic solvents, with better efficacy and storage stability for azadirachtins.

All of the patents and publications mentioned throughout this application are incorporated herein in their entirety.

SUMMARY OF THE INVENTION

A feature of the present invention is to provide a storage stable pesticide formulation which avoids the use of organic solvent.

A further feature of the present invention is to provide a pesticide formulation which is storage stable.

An additional feature of the present invention is to provide a pesticide formulation which contains primarily all natural components and is an effective pesticide formulation.

Additional features and advantages of the present invention will be set forth in part in the description which follows, and in part will be apparent from the description, or may be learned by practice of the present invention. The objectives and other advantages of the present invention will be realized and obtained by means of the elements and combinations particularly pointed out in the written description and appended claims.

To achieve these and other advantages, and in accordance with the purpose of the present invention, as embodied and broadly described herein, the present invention relates to a storage stable pesticide formulation containing at least one vegetable oil, at least one non-ionic surfactant, and azadirachtin.

The present invention further relates to a storage stable pesticide formulation containing at least one vegetable oil, at least one surfactant, which is preferably non-ionic, and a neem extract which contains at least azadirachtin.

It is to be understood that both the foregoing general description and the following detailed description are exemplary and explanatory only and are intended to provide further explanation of the present invention, as claimed.

DETAILED DESCRIPTION OF THE PRESENT INVENTION

The present invention relates to a pesticide formulation containing at least one vegetable oil, at least one surfactant, and azadirachtin, which is preferably present in the form of a neem extract.

The pesticide formulations of the present invention are especially useful as concentrates or technical formulations which are storage stable and can be diluted, such as with water, to form a pesticide formulation that can be used on plants, trees, and the like. Typically, the concentrates of the present invention are diluted with water at a rate of from about 2.5 to 5 ml concentrate to 1 liter of water, and more preferably from about 3 to about 4 ml concentrate to 1 liter of water. Since the addition of water to azadirachtin containing formulations can be detrimental to the azadirachtin by causing degradation of the azadirachtin, the dilution generally occurs at the site of application. Diluting with water can cause the azadirachtin to be degraded such that the diluted formulation would need to be applied in approximately 3 days or less. While other solvents can be used, such solvents are expensive or detrimental to the environment. Thus, the present invention involves the preparation of the technical product or concentrate which can preferably be diluted with water (for instance, diluted by the user) and applied in an effective and safe manner.

The concentrate of the present invention preferably contains substantially no water, and more preferably less than about 2% by weight and even more preferably less than 1% or less than ½% by weight of water, based on the weight of the concentrate. Generally, if water is present in these low amounts, it will be present due to moisture formation in the sealed container and will not be the result of the intentional addition of water.

The azadirachtin is preferably at least azadirachtin A and/or B. Other forms of azadirachtin can be used alternatively or in combination with the preferred azadirachtins. For instance, other structurally related azadirachtins can be used such as C, D, E, F, G, H, I, J, and/or K, and the like. The neem seed extract which can be present in the pesticide formulation contains at least azadirachtin. Further, the neem seed extract can contain nimbin, salannin, azadiradone, and the like. Further, the neem seed extract can contain nimbin, salannin, azadiradone, and the like. For purposes of the present invention, azadirachtin includes one or more types of azadirachtins.

The amount of azadirachtin present in the pesticide formulation can be any amount effective to have insecticidal activity, such as, but not limited to, reducing or eliminating insecticidal damage to trees and/or crops. Preferably the amount of azadirachtin present in the pesticide formulation is from about 0.1 weight % to about 5.0 weight % based on the weight of the pesticide formulation, and more preferably from about 0.1% to about 1.0 weight % based on the weight of the pesticide formulation. In terms of the neem seed extract, the neem seed extract is preferably present in an amount, such that from about 0.1 to about 5.0 weight % of azadirachtin is present in the pesticide formulation. Most preferably, the azadirachtin present in the pesticide formulation is from about 0.1 to about 5.0 weight % azadirachtin A and/or B.

The method for producing the azadirachtin, which is storage stable, is described in U.S. Pat. No. 5,695,763, which is incorporated herein in its entirety. In general, the azadirachtin is recovered preferably from the seeds of a neem tree by crushing the seeds and then extracting the azadirachtin and other active ingredients from the crushed seeds with water. The extracting of azadirachtin and other active ingredients from the water is accomplished using a non-aqueous solvent which is not miscible with water and has a high solubility of azadirachtin than water, or by using a surfactant having a turbidity temperature between 20° and 80° C. The concentrated azadirachtin is then recovered from the second extracting solution. The azadirachtin containing solution is then concentrated to produce an azadirachtin concentrate which is added to a liquid hydrocarbon, thus forming an azadirachtin precipitate that is then recovered for use in pesticide formulations. The method described in Indian Patent No. 181,845 can be also used for the preparation of azadirachtin containing extracts. The azadirachtin can also be recovered by the techniques set forth in U.S. Pat. Nos. 4,556,562 and 5,124,349 and other conventional methods.

With respect to the vegetable oil, the vegetable oil is preferably present in an amount of about 60 weight % or less by weight of the pesticide formulation, and even more preferably is present in an amount of from about 20 weight % to about 50 weight % vegetable oil by weight of the pesticide formulation, and most preferably about 48 weight % vegetable oil, by weight of the pesticide formulation. The vegetable oil is preferably sesame seed oil. Mixtures of two or more types of vegetable oils can be used.

With respect to the surfactant, the surfactant is preferably a non-ionic surfactant. Most preferably, the surfactant is a Sorbitan trioleate and even more preferably is a polyoxyethylene sorbitan trioleate such as polyoxyethylene 20 sorbitan trioleate which is sold under the trade name Tween® 85 which is a non-ionic surfactant manufactured by ICI Limited. The surfactant can be present in any amount as long as the azadirachtin and vegetable oil are uniformly dispersed throughout the pesticide formulation and the surfactant does not significantly hinder the insecticidal activity of the active ingredients. Preferably, the surfactant is present in an amount of from about 20 weight % to about 55 weight %, by weight of the pesticide formulation, and even more preferably is present in an amount of from about 40% to about 50% by weight, and most preferably is present in an amount of from about 48 to about 50 weight %. Mixtures of two or more different types of surfactants can be used.

These pesticide formulations can be prepared by conventional mixing techniques such as by adding the ingredients together and mixing the ingredients with conventional mixers. Preferably, the surfactant is added to the neem extract containing the azadirachtin. Then, sesame oil is added afterwards and the ingredients are mixed together to the extent that they are distributed uniformly throughout the formulation.

The behavior of azadirachtin in real time and in accelerated conditions (especially at 54° C.) is quite differ. The data generated on stability of azadirachtin A in a formulation indicated that the accelerated storage test over estimates the degradation of azadirachtin A in real time conditions. Under the accelerated storage test conditions (at 54° C.), the degradation of azadirachtin A was observed to be 66% after 14 days but under real time conditions at 20° C., a degradation of approximately 0.9% per month was observed with a total degradation of 11% per year. Thus, for instance, the formulation (Formulation III, Example 2) as per the present invention can expect to have higher stability as it recorded only 35.35% degradation in 14 days at 54° C.

The pesticide formulations of the present invention, and preferably the concentrates, are preferably quite storage stable and thus very beneficial for commercial applications. Preferably, the pesticide formulations of the present invention have a stability such that at least 90% by weight of the azadirachtin originally present remains after 1 year of storage at 25° C. in a sealed container. Most preferably, the pesticide formulations of the present invention are storage stable to the extent that at least 90% by weight of the azadirachtins originally present remain after 1 year of storage at room temperature in a sealed container.

The ability of the pesticide formulations of the present invention to contain no organic solvents and yet be storage stable has advantages over commercially available formulations since in many specialty applications, the use of organic solvents is not recommended.

Other embodiments of the present invention will be apparent to those skilled in the art from consideration of the specification and practice of the invention disclosed herein. It is intended that the specification and examples be considered as exemplary only, with a true scope and spirit of the present invention being indicated by the following claims and equivalents thereof.

EXAMPLES

1. Preparation of Azadirachtin Formulations

The dry neem seed extracts of azadirachtin used for the preparation of various formulations were prepared according to the method described in Indian Patent No. 181,845. The neem seed extract powders normally contained 30–45% by weight of azadirachtin (A, 25–35% and B, 5–9%). One of the samples containing 40.26% by weight of azadirachtin (A, 31.51% and B, 8.75%) was used in the preparation of the following formulations. Analysis of azadirachtin content of all the samples and formulations was by HPLC using an external, analytically pure azadirachtin standard, following the method described by Kleeberg (1994).

Formulation I: 3.103 g of the neem seed extract powder containing azadirachtin was added slowly to a well stirred liquid of Tween 85 surfactant (96.90 g) in a conical flask and stirring was continued for 30 minutes until a clear homogeneous mixture was obtained. The azadirachtin content of the formulation was found to be 1.24% by weight.

Formulation II: 3.1 g of the neem seed extract powder containing azadirachtin was added slowly to a well stirred liquid of Tween 85 surfactant (72.00 g) in a conical flask and stirring was continued for 30 minutes until the solid was completely dissolved. To this, sesame oil was added (25.04 g) and the contents were mixed thoroughly to obtain a clear homogeneous formulation. The azadirachtin content of the formulation was found to be 1.27% by weight.

Formulation III: 3.15 g of the neem seed extract powder containing azadirachtin was added slowly to a well stirred liquid of Tween 85 surfactant (48.86 g) in a conical flask and stirring was continued for 45 minutes until the solid was completely dissolved. To this, sesame oil was added (48.0 g) and the contents were stirred thoroughly to obtain a clear homogeneous formulation. The azadirachtin content of the formulation was found to be 1.24% by weight.

Formulation IV: 3.11 g of the neem seed extract powder containing azadirachtin was added slowly to a well stirred liquid to Tween 85 surfactant (22.03 g) in a conical flask and stirring was continued for about 60 minutes until the solid was completely dissolved. To this, sesame oil was added (75.03 g) and the contents were stirred for 20 minutes. The formulation was found to be non-homogeneous at this proportion of Tween 85 surfactant and sesame oil and the layers of surfactant and oil were separated upon standing. The individual layers thus obtained were separated with the help of a separating funnel. The sesame oil fraction containing 0.26% by weight of azadirachtin was used for evaluation of stability of azadirachtin in sesame oil.

Formulation V: 3.11 g of the neem seed extract powder containing azadirachtin was added slowly to a well stirred solution of Tween 85 surfactant (32.24 g) and cyclohexanone (32.36 g) in a conical flask and stirring was continued for 30 minutes until the solid completely dissolved. To this, neem oil was added (32.20 g) and the contents were stirred thoroughly to obtain a clear homogeneous formulation. The azadirachtin content of the formulation was found to be 1.25% by weight.

2. Stability of Azadirachtin Formulations Containing Sesame Oil

The stability of formulations I–IV obtained by Example 1 were studied at 54° C. Each of the samples (20 g) were stored into a sealed glass vial and kept in the oven at 54° C. for 28 days. Samples were taken out every week and analyzed for azadirachtin content using HPLC. The results (Table 1) indicate that a higher stability for azadirachtin was achieved in formulations II and III compared to the rest of the formulations.

TABLE 1

| Formu-lation | Initial Azadirachtin, A & B content | | | % Degradation of Azadirachtin A & B at 54° C. | | | | | |
|---|---|---|---|---|---|---|---|---|---|
| | (%) | | | 7 days | | 14 Days | | 28 Days | |
| | A | B | A & B | A | B | A | B | A | B |
| I | 0.96 | 0.27 | 1.23 | 47.87 | Nil | 68.25 | 3.70 | 83.07 | 3.70 |
| II | 0.99 | 0.28 | 1.27 | 45.45 | — | 59.60 | 3.57 | 75.76 | 3.57 |
| III | 0.99 | 0.28 | 1.27 | 25.25 | Nil | 35.35 | Nil | 52.52 | 3.57 |
| IV | 0.18 | 0.08 | 0.26 | 11.11 | Nil | 27.77 | Nil | 50.00 | 12.5 |

3. Antifeedant Effect of Azadirachtin Formulations Containing Sesame Oil and Neem Oil Against *Spodoptera litura*

Formulations I–III and V were tested for their antifeedant effect against the insect *Spodoptera litura*. The castor leaf disks were cut and dipped in 30 and 50 ppm of azadirachtin concentrations of different formulations and offered to 5 day old *S. litura* larvae. The experiments were replicated three times with ten insects per treatment per replication. The percentage antifeedancy was assessed after 2, 5, 10, and 14 days after treatment by calculating the difference in leaf area consumed in the treated and control group. Formulation III with 48% by weight of sesame oil showed higher antifeedant activity.

TABLE 2

| | | % Antifeedancy | | | |
|---|---|---|---|---|---|
| Treatments Aza (ppm) | Days after Treatment | Formu-lation I | Formu-lation II | Formu-lation III | Formu-lation V |
| 30 | 2 | 33.9 c | 46.17 b | 60.53 a | 43.56 b |
| | 5 | 66.41 b | 71.17 b | 89.67 a | 70.23 b |
| | 10 | 91.90 d | 94.90 b | 96.94 a | 93.86 c |
| | 14 | 89.63 b | 96.57 a | 97.13 a | 93.79 c |
| 50 | 2 | 53.12 ab | 49.34 ab | 66.02 a | 36.56 b |
| | 5 | 72.36 b | 74.27 b | 92.09 a | 69.29 b |
| | 10 | 95.25 c | 95.78 b | 95.25 c | 94.05 d |
| | 14 | 92.49 d | 95.49 a | 92.49 d | 94.02 c |

Mean values in a row followed by the same letter means the values are similar and have no significant difference (p < 0.001) Duncan Multiple Range Test (DMRT).

4. Growth Inhibition Effect of Azadirachtin Formulations Containing Sesame Oil and Neem Oil Against *Spodoptera litura*

The insect growth inhibition active of formulations I–III and IV were tested against the insect *S. litura*. The castor leaves, treated with 30 and 50 ppm of azadirachtin concentration of various formulations, were offered to 5 day old *S. litura* larvae. The experiments were conducted using ten insects per treatment and replicated three times. Growth inhibition was assessed 2, 5, 7, 10, and 14 days after treatments by weighing the larvae. The mean weights for each treatment group were expressed as a percentage of controls. Formulation III containing 48% by weight of sesame oil again showed the highest growth inhibitory activity against the insect *Spodoptera litura* (Table 3).

TABLE 3

| | | % Growth Inhibition | | | |
|---|---|---|---|---|---|
| Treatments Aza (ppm) | Days after Treatment | Formu-lation I | Formu-lation II | Formu-lation III | Formu-lation V |
| 30 | 2 | 32.9 a | 39.4 a | 52.5 a | 37.3 a |
| | 5 | 63.9 ab | 65.3 ab | 59.8 ab | 65.4 ab |
| | 7 | 87.6 d | 89.6 bc | 90.6 b | 89.2 c |
| | 10 | 91.5 f | 94.4 d | 96.3 b | 93.8 e |
| 50 | 2 | 45.2 a | 53.1 a | 48.1 a | 38.4 a |
| | 5 | 69.2 ab | 74.3 ab | 68.5 a | 61.8 ab |
| | 7 | 90.9 d | 90.9 b | 92.6 a | 90.3 bc |
| | 10 | 95.3 c | 96.2 b | 98.0 a | 94.9 c |

Mean values in a row followed by the same letter are statistically not significant (p < 0.001) DMRT.

5. Mortality Effect of Azadirachtin Formulations Containing Sesame Oil and Neem Oil Against *Spodoptera litura*.

The insecticidal (mortality) activity of azadirachtin formulations (I–III and V) was studied against the insect *Spodoptera litura*. For the mortality test, castor leaves treated with 30 and 50 ppm concentrations of azadirachtin of various formulations were offered to 5 day old *S. litura* larvae. The experiments were replicated three times with 10 insects per treatment per replication. The percentage mortality was assessed after 5, 7, 10, and 14 days after treatment. The efficacy date (Table 4) indicates that Formulation III containing 48% by weight of sesame oil again showed the highest overall mortality against the insect *Spodoptera litura*.

TABLE 4

| | | % Mortality | | | |
|---|---|---|---|---|---|
| Treatments Aza, (ppm) | Day | Formu-lation I | Formu-lation II | Formu-lation III | Formu-lation V |
| 30 | 5 | 0.0 c | 6.7 b | 20.0 a | 10.0 b |
| | 7 | 15.8 b | 26.7 c | 32.5 bc | 16.7 d |
| | 10 | 27.5 c | 41.7 bc | 43.3 b | 35.8 bc |
| | 14 | 69.7 e | 93.3 d | 96.3 b | 78.4 d |
| 50 | 5 | 0.0 c | 10.0 b | 23.3 a | 24.1 a |
| | 7 | 10.0 b | 43.3 ab | 50.8 a | 35.0 bc |
| | 10 | 40.8 bc | 50.8 b | 66.7 a | 38.3 bc |
| | 14 | 80.1 d | 96.7 b | 100.0 a | 93.0 c |

Mean values in a row followed by the same letter are statistically not significant (p < 0.001) DMRT.

What is claimed is:

1. A storage stable pesticide formulation comprising from about 1% to about 60% by weight of at least one vegetable oil, from about 20% to about 55% by weight of at least one non-ionic surfactant, based on the weight of the pesticide formulation, and a neem seed extract, wherein said neem seed extract comprises from about 1% to about 5% by weight azadirachtin based on the weight of the pesticide formulation, wherein said at least one non-ionic surfactant is a sorbitan polyoxyethylene trioleate, wherein said at least one vegetable oil is sesame seed oil, and wherein said formulation contains less than about ½% by weight water, based on the weight of the formulation, wherein said formulation is storage stable such that at least 90% by weight of the azadirachtin originally present remains after 1 year of storage at 25° C. in a sealed container, or such that at least at about 25 wt % of the azadirachtin A originally present remains after an accelerated aged test of 28 days at 54° C. in a sealed container and wherein said formulation is free of organic solvents.

2. The formulation of claim 1, wherein said vegetable oil contains less than 1% by weight free fatty acid based on the weight of the vegetable oil.

3. The formulation of claim 1, wherein said azadirachtin is azadirachtin A, azadirachtin B, or both.

4. The formulation of claim 1, wherein said formulation is storage stable such that at least 90% by weight of the azadirachtin originally present remains after 1 year of storage at 25° C. in a sealed container.

5. The formulation of claim 1, wherein said vegetable oil is present in an amount of from about 20 weight % to about 50 weight %; and said surfactant is present in an amount of from about 40 weight % to about 50 weight %.

\* \* \* \* \*